US00PP36825P2

(12) United States Plant Patent
Koot

(10) Patent No.: US PP36,825 P2
(45) Date of Patent: Jul. 15, 2025

(54) ***BUDDLEJA* PLANT NAMED 'Botex 010'**

(50) Latin Name: *Buddleja davidii*
Varietal Denomination: Botex 010

(71) Applicant: Johannes Adrianus Maria Koot, Kaatsheuvel (NL)

(72) Inventor: Johannes Adrianus Maria Koot, Kaatsheuvel (NL)

(73) Assignee: BOTANIC EXPERIENCE B.V., Kaatsheuvel (NL)

( * ) Notice: Subject to any disclaimer, the term of this patent is extended or adjusted under 35 U.S.C. 154(b) by 0 days.

(21) Appl. No.: 18/912,712

(22) Filed: Oct. 11, 2024

(51) Int. Cl.
*A01H 5/02* (2018.01)
*A01H 6/00* (2018.01)

(52) U.S. Cl.
USPC ..... Plt./242

(58) Field of Classification Search
USPC ..... Plt./242
CPC ..... A01H 5/02; A01H 5/00; A01H 6/00
See application file for complete search history.

(56) References Cited

PUBLICATIONS

Greenhouse Product News Dummen Orange will setup 2024 Cast display at new location, retrieved on Jan. 27, 2025 at https://gpnmag.com/news/dummen-orange-will-setup-2024-cast-display-at-new-location/, 6 pp. (Year: 2024).*

Plantipp *Buddleja davidii* Little Rockstars Purple, retrieved on Jan. 27, 2025 at https://plantipp.eu/uk/varieties/buddleja-davidii-little-rockstars-purple-botex-010pbr, 2 pp. (Year: 2025).*

* cited by examiner

*Primary Examiner* — June Hwu
(74) *Attorney, Agent, or Firm* — Penny J. Aguirre

(57) ABSTRACT

A new cultivar of *Buddleja* plant named 'Botex 010' that is characterized by its very compact, dense, and a neat and naturally rounded plant habit, its flowers that are dark, vibrant purple in color, its suitability for growing in small containers, and its quick flowering with a very floriferous blooming habit.

3 Drawing Sheets

Botanical classification: *Buddleja davidii.*
Variety denomination: 'Botex 010'.

CROSS-REFERENCE TO RELATED APPLICATIONS

This application is related to a European Community Plant Variety Office (CPVO) Plant Breeder's Rights Application No. 2023/1784 filed on Sep. 13, 2023, under 35 U.S.C. 119(f). The Applicant received the information for the Plant breeders' rights application directly from the Inventor. This application is also co-pending with a U.S. Plant Patent Applications filed for plants derived from the same breeding program that are entitled *Buddleja* Plant Named 'Botex 001' (U.S. Plant Pat. No. 34,515) and *Buddleja* Plant Named 'Botex 008' (U.S. Plant Pat. No. 36,578), *Buddleja* Plant Named 'Botex 009' (U.S. Plant Pat. No. 36,579), *Buddleja* Plant Named 'Botex 011' (U.S. Plant patent application Ser. No. 18/912,725), *Buddleja* Plant Named 'Botex 012' (U.S. Plant Pat. No. 36,649), *Buddleja* Plant Named 'Botex 013' (U.S. Plant Pat. No. 18/912,731).

BACKGROUND OF THE INVENTION

The present invention relates to a new and distinct cultivar of *Buddleja davidii* will be referred to hereafter by its cultivar name, 'Botex 010'. 'Botex 010' is a new shrub grown for use as an ornamental landscape plant and as a container plant.

The new cultivar of *Buddleja* is a selection from an ongoing breeding program conducted by the Inventor in Kaatsheuvel, The Netherlands with the goal of creating new cultivars of *Buddleja* with very neat and compact plant habits with suitability for growing in small containers combined with unique vibrant flower colors and floriferous blooming habits.

The Inventor made a cross in July of 2019 between unnamed and unpatented proprietary plants in the Inventor's breeding program; reference no. 19-016-01 as the female parent and reference no. 18-008-01 as the male parent. The Inventor selected 'Botex 010' in August of 2022 as a single unique plant amongst the seedlings that resulted from the above cross.

Asexual propagation of the new cultivar was first accomplished by the Inventor using stem cuttings in Kaatsheuvel, The Netherlands in 2022. Asexual propagation by stem cuttings has determined that the characteristics of the new cultivar are stable and are reproduced true to type in successive generations.

SUMMARY OF THE INVENTION

The following traits have been repeatedly observed and represent the characteristics of the new cultivar. These attributes in combination distinguish 'Botex 010' as a unique cultivar of *Buddleja.*

1. 'Botex 010' exhibits a very compact, dense, and a neat and naturally rounded plant habit.
2. 'Botex 010' exhibits flowers that are dark, vibrant purple in color.
3. 'Botex 010' exhibits suitability for growing in small containers.

4. 'Botex 010' exhibits quick flowering with a very floriferous blooming habit.

The female parent of 'Botex 010' differs from 'Botex 010' in having longer inflorescences, taller plant height, and flowers that are pink-red in color. The male parent of 'Botex 010' differs from 'Botex 010' in having flowers that are more bluish purple in color, shorter inflorescences, and a shorter plant height. 'Botex 010' can be compared to the *Buddleja* cultivars 'Black Knight' (not patented) and 'Botex 001'. 'Black Knight' differs from 'Botex 010' in having a taller plant height, a more open plant habit, inflorescences that are less compact and longer, and flowers that are darker purple in color. 'Botex 001' differs from 'Botex 010' in having flowers that are blue-violet in color, a less dwarf plant habit, and larger leaves.

'Botex 010' can also be compared to the co-pending cultivars of *Buddleja*; 'Botex 008', 'Botex 009', 'Botex 011', 'Botex 012', and 'Botex 013'. 'Botex 008' differs from 'Botex 010' in having flowers that are magenta purple in color and in being taller in height. 'Botex 009' differs from 'Botex 010' in having flowers that are fuchsia pink in color. 'Botex 011' differs from 'Botex 010' in having flowers that are light pink in color. 'Botex 012' differs from 'Botex 010' in having flowers that are light violet blue in color. 'Botex 013' differs from 'Botex 010' in having flowers that are white with orange centers in color.

STATEMENT REGARDING PRIOR DISCLOSURES BY THE INVENTOR

The Applicant asserts that no publications or advertisements relating to sales, offers for sale, or public distribution occurred more than one year prior to the effective filing date of this application. Any information about the claimed plant would have been obtained from a direct or indirect disclosure from the Inventor. The Applicant claims a prior art exemption under 35 U.S.C. 102(b)(1) for disclosures and/or sales that fall within a one-year grace period to the filing date. Disclosures include website listings by 27East, Dummen Orange, Cool Plants, Floral Daily, Bill Moore & Co., Ball Seed, Substack, National Garden Bureau, Visions Pictures, University of Georgia Trial Gardens, Garden Center Magazine, Baldur-Netherland, Plantenkwekerij Vechtdal, Dobrepole, Sweet Garden, and Zahradnictvi-spomysl.

BRIEF DESCRIPTION OF THE DRAWINGS

The accompanying color photographs illustrate the overall appearance and distinct characteristics of the new *Buddleja*. The photographs were taken of a one-year-old plant as grown in a greenhouse in a 19-cm container in Kaatsheuvel, The Netherlands.

The photograph in FIG. 1 provides a side view of the overall plant habit of 'Botex 010' in bloom.

Figure 1:
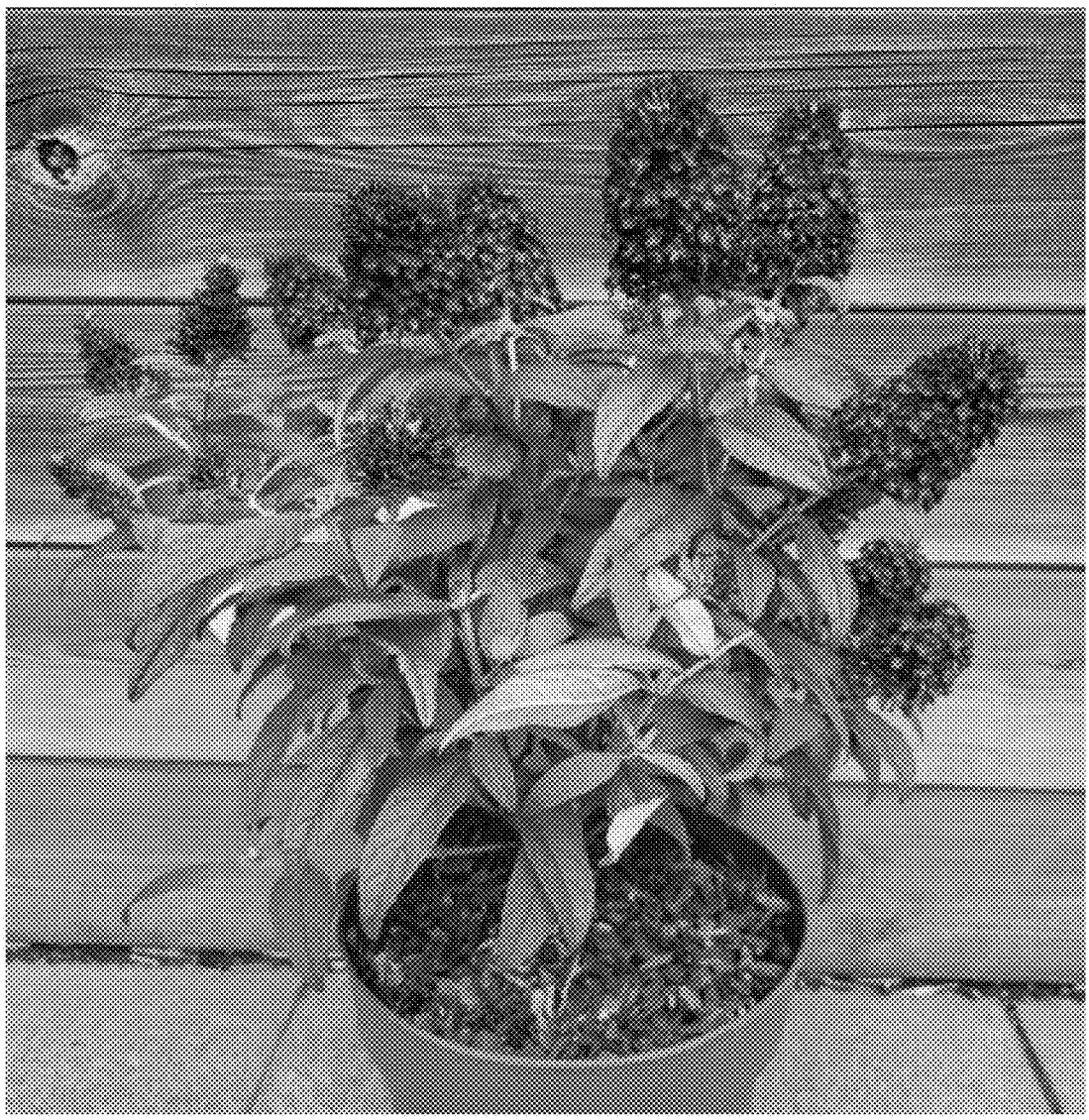
Figure 2:
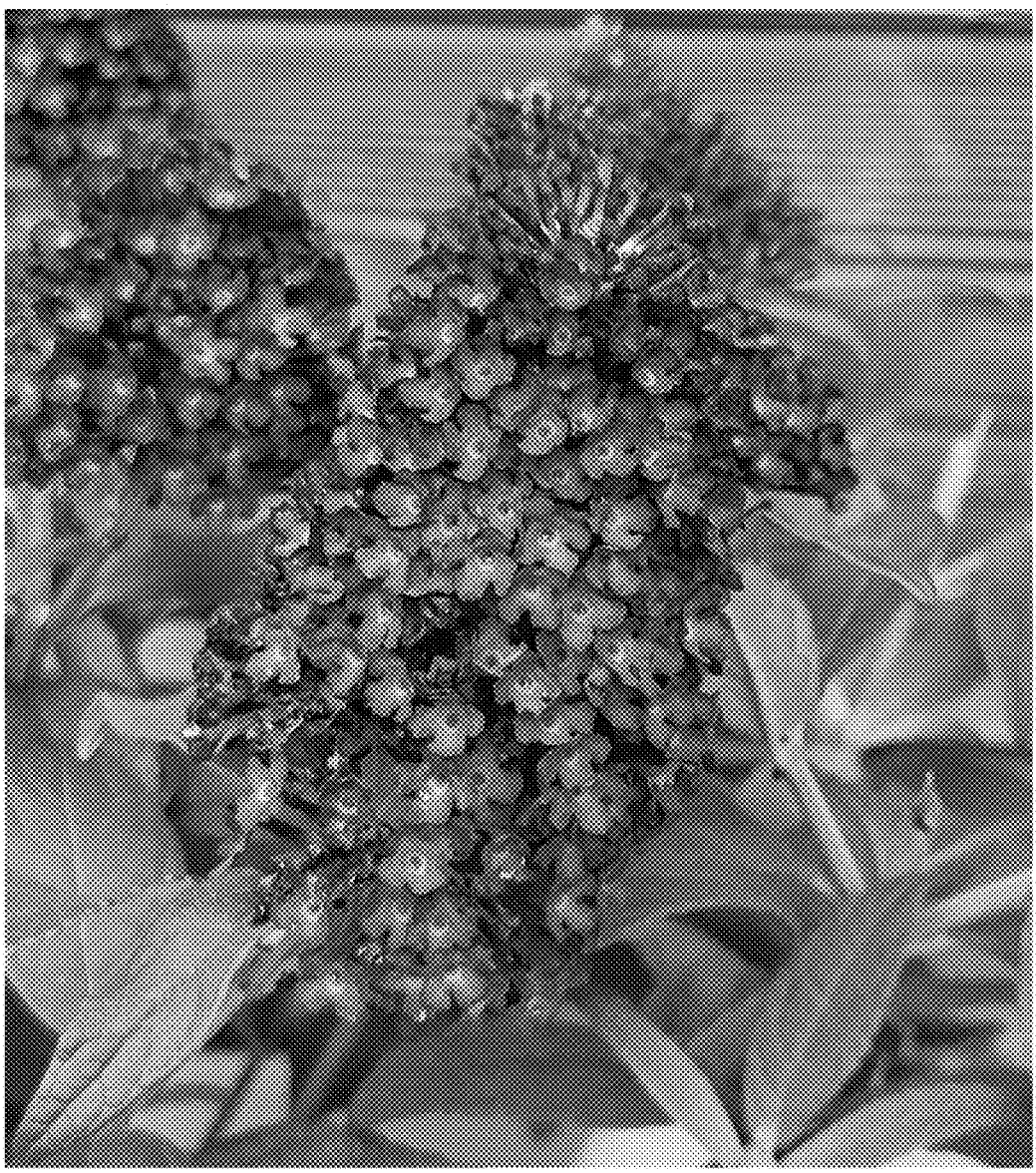

The photograph in FIG. 2 provides a close-up view of an inflorescence of 'Botex 010'.

Figure 3:
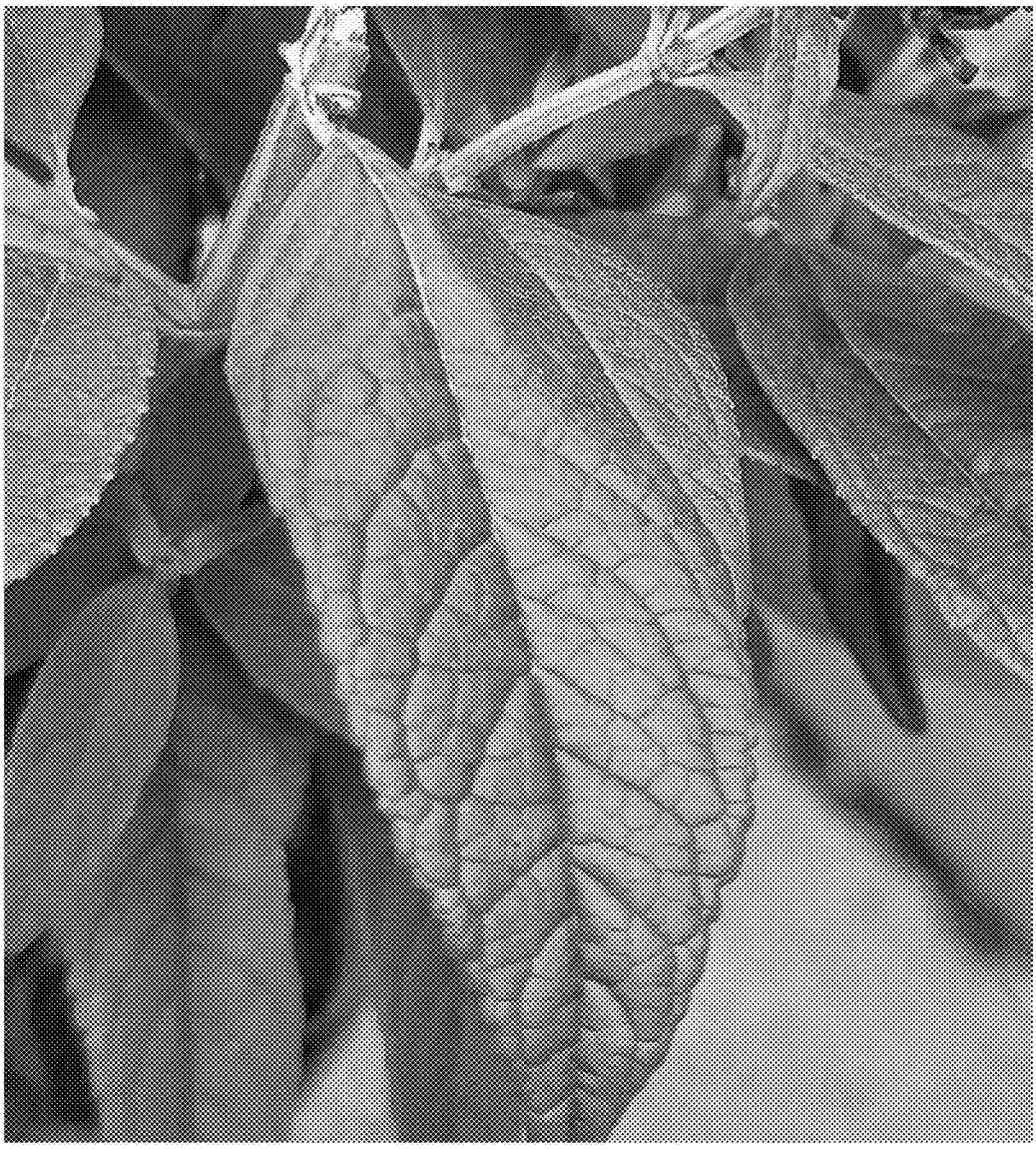

The photograph in FIG. 3 provides a close-up view of a leaf of 'Botex 010'.

The colors in the photographs are as close as possible with the photographic and printing technology utilized and the color values cited in the Detailed Botanical Description accurately describe the colors of the new *Buddleja*.

DETAILED BOTANICAL DESCRIPTION

The following is a detailed description of one-year-old plants as grown in a greenhouse in 19-cm containers in Kaatsheuvel, The Netherlands. The phenotype of the new cultivar may vary with variations in environmental, climatic, and cultural conditions, as it has not been tested under all possible environmental conditions. The color determination is in accordance with The 2015 Colour Chart of The Royal Horticultural Society, London, England, except where general color terms of ordinary dictionary significance are used.

General description:

*Blooming period*.—July to October in The Netherlands.

*Plant type*.—Deciduous perennial shrub.

*Plant habit*.—Very compact, upright and naturally rounded, dense.

*Plant size*.—An average of 32 cm in height and 35 cm in width as a one-year-old plant in a container and reaches 50 cm in height and in spread as grown in the landscape.

*Cold hardiness*.—At least in U.S.D.A. Zone 5.

*Diseases and pests*.—No susceptibility and resistance to diseases or pests has been observed.

*Propagation*.—Stem cuttings.

*Root description*.—Fibrous.

*Root development*.—4 to 5 weeks to initiate roots and 6 to 7 weeks to fully root as a young plant in a P9 container.

*Growth rate*.—Vigorous, quick finishing.

Branch description:

*Branch shape*.—Quadrangular.

*Branch color*.—Young stems; 145B, mature and older woody stems; 199A.

*Branch strength*.—Strong.

*Branch size*.—Up to 22 cm in length and 4 mm in diameter.

*Branch surface*.—Medium pubescence.

*Branch aspect*.—Lateral stems held upright to an average angle of 30° to vertical.

*Branch internode length*.—Average of 2.5 cm.

*Branching*.—1 main branch, 6 secondary branches.

Foliage description:

*Leaf shape*.—Narrowly elliptical to elliptical.

*Leaf division*.—Simple.

*Leaf base*.—Attenuate.

*Leaf apex*.—Acute.

*Leaf fragrance*.—None.

*Leaf venation*.—Pinnate, veins match surface colors, midrib on both surfaces 145B in color.

*Leaf margins*.—Serrate.

*Leaf arrangement*.—Opposite.

*Leaf attachment*.—Petiolate.

*Leaf surface*.—Both sides are smooth, matte, and pubescent, medium bulging between veins.

*Leaf size*.—Up to 7 cm in length and an average of 2.6 cm in width.

*Leaf quantity*.—An average of 12 per main stem.

*Leaf color*.—Upper surface young and mature; 137B, young lower surface; 191A, lower surface mature; 191D.

*Petioles*.—An average of 3 mm in length and 2 mm in diameter, strong, surface slightly pubescent, color; young upper side 137B, young lower side 191A, mature upper side 137B, mature lower side 191D.

Inflorescence description:

*Inflorescence type*.—Compound terminal and axial panicles, held upright.

*Inflorescence size*.—Up to 6 cm in height, up to 4.3 cm in width.

*Inflorescence shape*.—Cylindrical.

*Flower fragrance*.—Sweet, pleasant and medium strength.

*Lastingness of flowers*.—An average of 5 days, persistent.

*Flower buds*.—Oblong in shape, average of 5 mm in length and 1 mm in diameter, color; 86A.

*Flower aspect*.—Upright, slightly outward.

*Flower quantity*.—Average of 200 flowers per inflorescence and 16 inflorescences.

*Density of flowers per inflorescence*.—Dense.

*Flower type*.—Single, salverform.

*Flower surface*.—All surfaces glabrous and matte.

*Flower size*.—An average of 1.1 cm in height, 5 mm in diameter, flower throat; 3 mm in length, 1 mm in diameter, flower tube; 6 mm in length, 1 mm in diameter.

*Peduncles*.—Primary; an average of 1 cm in length and 3 mm in diameter, secondary; an average of 1 cm in length and 3 mm in diameter, 145C in color, strong, glossy and pubescent surface.

*Pedicels*.—An average of 2 mm in length and 1 mm in diameter, 145B in color, strong, surface is pubescent.

*Calyx*.—Campanulate in shape, an average of 3 mm in length and 1 mm in diameter.

*Sepals*.—4, 1 whorl, rotate arrangement, fused into a campanulate shape, 3 mm in length, <1 mm in width, lanceolate in shape, acute apex, fused base, entire margin, both surfaces are matte and slightly pubescent, color; when opening and fully open upper and lower surface 145C.

*Petals*.—Average of 4, rotate, fused into salverform, 1 whorl, roughly spathulate in shape, slightly undulate margin, rounded apex, an average of 3 mm in length and 3mm in width, color: petals; young upper and lower surface N81A, margins 83B, mature upper and lower N74A, margins N89A, throat; young inside and outside N81A, fading to N88A, mature outside 83B, fading to N88A, mature inside 25A, base 12A.

Reproductive organs:

*Gynoecium*.—4 pistils, 3 mm in length, style; an average of 2 mm in length, 145D in color, stigma; elongated, 1 mm in length and 145B in color, ovary is 145D in color.

*Androecium*.—Stamens; 4, filament; 4 mm in length, 20B in color, anther; ovate in shape, 1 mm in length, 11D in color, pollen; low in quantity, too little to measure color.

*Fruit and seed*.—No seeds or fruit observed to date.

It is claimed:

1. A new and distinct cultivar of *Buddleja* plant named 'Botex 010' as herein illustrated and described.

* * * * *